US00PP35023P2

(12) United States Plant Patent
Clark

(10) Patent No.: US PP35,023 P2
(45) Date of Patent: Mar. 7, 2023

(54) ***COLEUS* PLANT NAMED 'UF19-42-14'**

(50) Latin Name: *Coleus scutellarioides*
Varietal Denomination: UF19-42-14

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 10 days.

(21) Appl. No.: 17/803,412

(22) Filed: Jun. 24, 2022

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

(56) References Cited

U.S. PATENT DOCUMENTS

PP27,126 P3 8/2016 Clark et al.

*Primary Examiner* — Susan McCormick Ewoldt
(74) *Attorney, Agent, or Firm* — Katherine Koenig; Koenig IP Works, PLLC

(57) ABSTRACT

A new and distinct cultivar of *Coleus* (*Coleus scutellarioides*) plant named 'UF19-42-14', selected for having a combination of desirable traits that make it well-suited for good performance as an annual plant in the summer landscape. 'UF19-42-14' has contrasting yellow green leaf color with prominent dark purplish red veins, and excellent overall plant vigor in all trials. 'UF19-42-14' maintains its foliage late into the Fall season until frost. It has a very stable leaf color in both sun and shade and was well-branched and vigorous in all locations trialed. Due to its striking color combination and vigorous upright and spreading habit, this plant will likely be grown in landscapes as a specimen annual plant filling a large amount of space with color in a very short period of time.

3 Drawing Sheets

Genus and species: *Coleus scutellarioides*.
Cultivar denomination: 'UF19-42-14'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF19-42-14'. The new cultivar 'UF19-42-14' originated from an open pollination conducted in May-November 2018 in Gainesville, Fla. between the female *Coleus* plant 'UF18-38-14' (unpatented) and an unknown male *Coleus* plant. A single seedling was chosen in May 2019 for further asexual propagation in Gainesville, Fla.

The new cultivar 'UF19-42-14' has been reproduced asexually for over 18 months through meristem tip cuttings and has been found to retain its distinctive characteristics through successive asexual propagations. 'UF19-42-14' was first propagated asexually by meristem tip cuttings in May 2019 in Gainesville, Fla., and has remained true-to-type since that time.

Plant Breeder's Rights for the new cultivar 'UF19-42-14' have not been applied for, and 'UF19-42-14' has not been made publicly available more than one year prior to the filing date of this application.

When compared to the female parent 'UF18-38-14', which has leaves that are almost twice as long as they are wide, the new cultivar 'UF19-42-14' has smaller leaves that are almost equally wide as they are long. Leaves on 'UF19-42-14' are bright yellow green with prominent dark purplish red venation patterning throughout the leaf, whereas leaves from the female parent 'UF18-38-14' are solid maroon with a distinct chartreus margin. 'UF19-42-14' has a vigorous upright and spreading habit that is well-branched, whereas 'UF18-38-14' is much less vigorous, and more upright in habit with less lateral branching.

The new cultivar 'UF19-42-14' was selected because it has unique plant form, growing almost twice as wide as it grows tall. It has a striking foliage color and has not been observed to produce flowers in any field or greenhouse. It performs well in sun and shade and has excellent vigor to withstand the harsh selection conditions our plants are subjected to in full sun trials in Gainesville, Fla. 'UF19-42-14' is exceptional because it maintained its foliage color patterning in all trialing conditions tested.

SUMMARY OF THE INVENTION

The new cultivar 'UF19-42-14' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF19-42-14' when grown under normal horticultural practices in Gainesville, Fla. 'UF19-42-14' has the combination of vigorous upright and spreading growth habit, excellent heat tolerance, and consistent yellow green leaves with prominent dark purplish red venation that are significantly different than other *Coleus* plants. It has superior stability in foliage color in both sun and shade conditions, maintaining stable color in all conditions. It has excellent lateral branching, making it suitable for propagators and producers. 'UF19-42-14' has been observed to have long-season performance in landscape trials in Gainesville, Fla.

DESCRIPTION OF THE FIGURES

This new *Coleus* cultivar 'UF19-42-14' is illustrated by the accompanying photographs, which show the plant's form and foliage. The colors shown are as true as can be reasonably obtained by conventional photographic procedures.

FIG. 2 shows the growth habit, form, and foliage of the claimed plant; and

FIG. 3 shows a close-up view of the foliage of the claimed plant.

DETAILED BOTANICAL DESCRIPTION OF THE CULTIVAR

Figure 1:
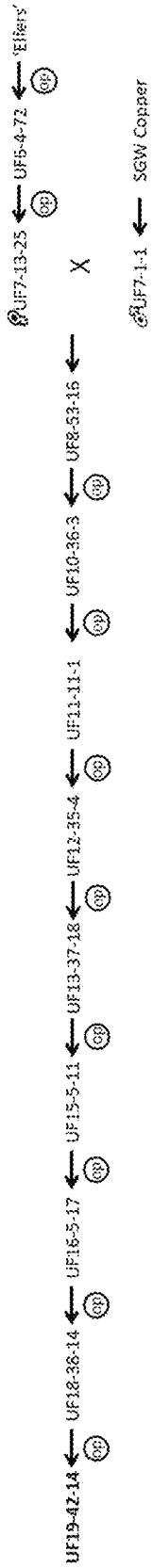
FIG. 1 shows the pedigree of the claimed plant.
Figure 2:
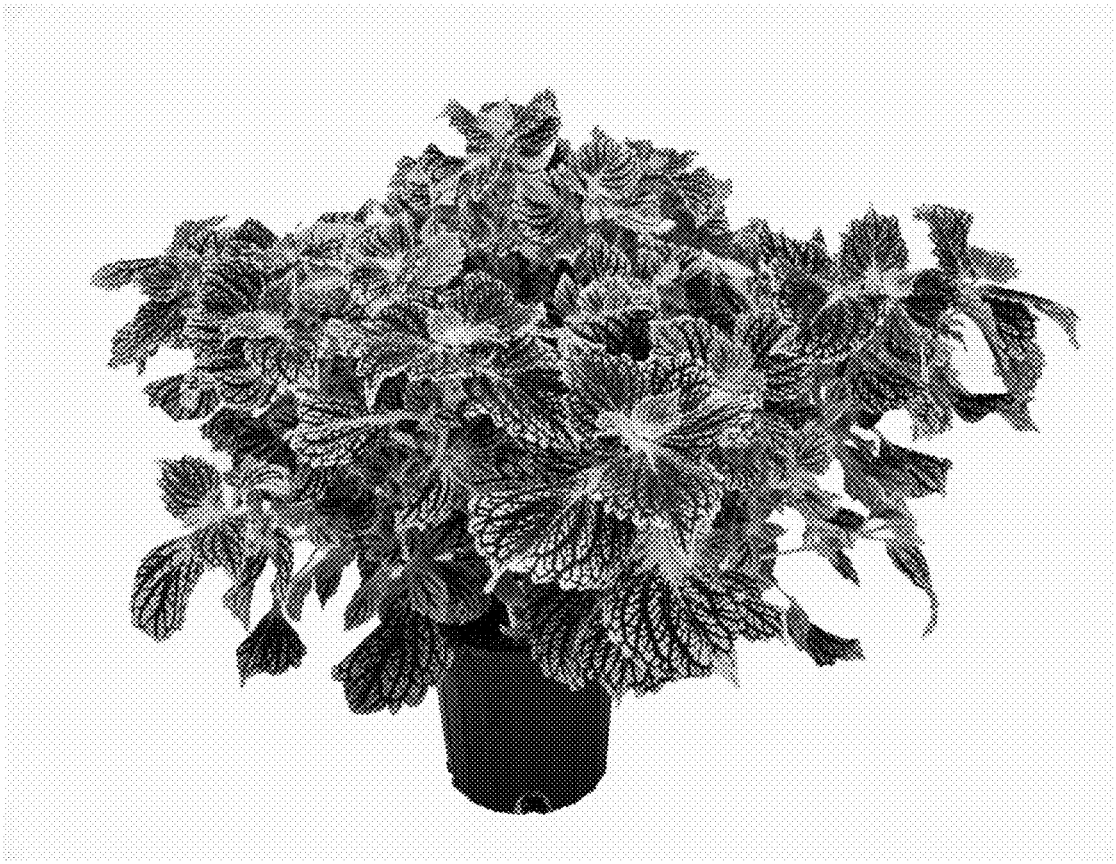
FIGS. 2 and 3 were taken from plants grown nine weeks from unrooted cuttings in September-November 2021 in a glass-covered greenhouse in Gainesville, Fla.
Figure 3:
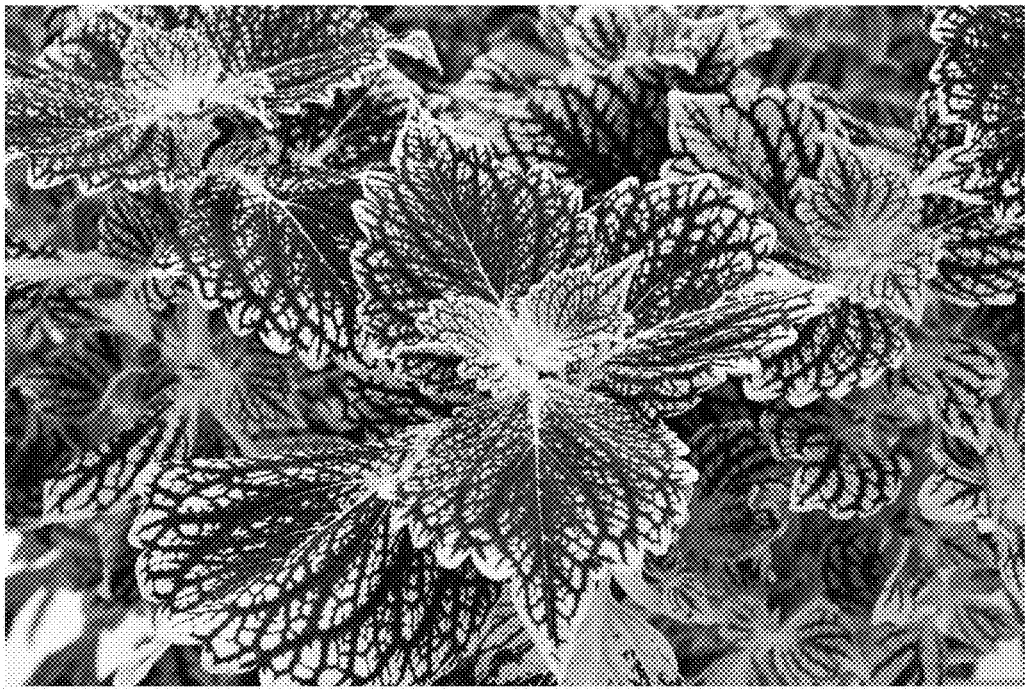

The following detailed description sets forth the distinctive characteristics of the new cultivar 'UF19-42-14'. Color references are to The R.H.S. Colour Chart of The Royal Horticultural Society of London (R.H.S.), 2007 (5th Edition).

Description of Growing Conditions

The detailed description was generated using nine-week-old plants of the new cultivar 'UF19-42-14' grown from unrooted cuttings in September-November 2021 in a glass-covered greenhouse in Gainesville, Fla. The plants were propagated in mist for ten days after cuttings were stuck, then grown in one-gallon pots for approximately seven and a half additional weeks.

BOTANICAL DESCRIPTION

Botanical classification:
- *Family*.—Lamiaceae.
- *Botanical name*.—*Coleus scutellarioides*.
- *Common name*.—*Coleus*.
- *Cultivar*.—'UF19-42-14'.

Parentage:
- *Female or seed parent*.—'UF18-38-14'.
- *Male or pollen parent*.—Unknown.

Plant description:
- *Growth habit*.—Upright and spreading.
- *Plant height* (*from top of soil*).—45-50 cm.
- *Plant width* (*horizontal plant diameter*).—75-80 cm.

Propagation:
- *Type cuttings*.—Vegetative meristem tip cuttings having at least 1 node.
- *Time to initiate roots*.—3-4 days.
- *Time to produce a rooted cutting*.—7-10 days.

Roots:
- *Rooting habit*.—Fibrous.
- *Root description*.—Callus forms in 2-3 days, roots initiate in 3-4 days and become a highly branched cutting in 7-10 days.

Branches:
- *Quantity per plant*.—6-7.
- *Branch color*.—RHS 143A (strong yellow green).
- *Texture*.—Smooth.
- *Pubescence*.—Not present.
- *Stem description*.—Square-shaped stem, 1.1 cm in diameter at the soil line.
- *Branch diameter*.—0.8-0.9 cm at the base of a 45 cm long branch.
- *Branch length*.—43-45 cm.
- *Internode length*.—6-7 cm.
- *Anthocyanin*.—Not present.

Foliage description:
- *Quantity of leaves per branch*.—22-24.
- *Arrangement*.—Opposite.
- *Fragrance*.—Not fragrant.
- *Shape*.—Ovate.
- *Length*.—10-12 cm.
- *Width*.—9-11 cm.
- *Apex*.—Broadly acute.
- *Base*.—Attenuate.
- *Margin*.—Lobed.
- *Leaf texture*.—Top: Pulverulent. Bottom: Smooth.
- *Pubescence*.—Not present.
- *Venation color, mature leaf*.—Upper surface, proximal (base): RHS 143A (strong yellow green). Upper surface, distal (tip): RHS N186D (dark purplish red). Lower surface: RHS N186D (dark purplish red).
- *Venation color, immature leaf*.—Upper surface: RHS 187B (dark red). Lower surface: RHS 144C (strong yellow green).
- *Venation pattern*.—Upper surface: Reticulate. Lower surface: Reticulate.
- *Color, immature leaf*.—Upper surface, main/background: RHS N144C (strong yellow green). Lower surface: RHS 144C (strong yellow green).
- *Color, mature leaf*.—Upper surface, main/background: RHS 144A (strong yellow green). Lower surface, main/background: RHS 141C (strong yellowish green).
- *Petiole length*.—4-5 cm.
- *Petiole diameter*.—0.2-0.3 cm.
- *Petiole color*.—RHS 143B (strong yellow green).
- *Petiole texture*.—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. *Impatiens* Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronon-*

*spora lamii*). This pathogen has been observed in stock materials grown closely together in cooler growing seasons.

COMPARISON WITH KNOWN CULTIVARS

Plants of the new *Coleus* cultivar 'UF19-42-14' can be compared to those of 'UF10-45-12' (sold commercially under the trade name COLEOSAURUS™, U.S. Plant Pat. No. 27,126). The main background color on the upper surface of mature leaves of both 'UF19-42-4' and 'UF10-45-12' is RHS 144A (strong yellow green); however, 'UF19-42-14' has wider and less defined venation coloration of RHS 187B (dark red), whereas 'UF10-45-12' has narrower and more defined venation coloration of RHS 59A (dark red). Additionally, 'UF19-42-14' has leaf margins with lobes that are irregular in depth, whereas 'UF10-45-12' has leaf margins with lobes that are more consistent in depth.

What is claimed is:

1. A new and distinct *Coleus scutellarioides* plant named 'UF19-42-14' as shown and described herein.

* * * * *